(12) United States Patent
Deyette, Jr. et al.

(10) Patent No.: US 7,722,638 B2
(45) Date of Patent: May 25, 2010

(54) DELIVERY AND RETRIEVAL MANIFOLD FOR A DISTAL PROTECTION FILTER

(75) Inventors: Thomas Deyette, Jr., Hudson Falls, NY (US); Eric Houde, Saratoga Springs, NY (US); Scott A. Diamond, Fort Edward, NY (US); Mark H. VanDiver, Argyle, NY (US); Colin P. Hart, Queensbury, NY (US); Glenn H. Wadleigh, Queensbury, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 346 days.

(21) Appl. No.: 11/956,977

(22) Filed: Dec. 14, 2007

(65) Prior Publication Data

US 2008/0091229 A1    Apr. 17, 2008

Related U.S. Application Data

(63) Continuation of application No. 10/053,143, filed on Jan. 17, 2002, now abandoned.

(51) Int. Cl.
*A61M 29/00* (2006.01)

(52) U.S. Cl. ..................... 606/200; 623/1.11

(58) Field of Classification Search .......... 606/200, 606/110, 113, 114, 127, 128, 191–199, 86 A; 604/96.01–113, 523, 528; 285/114–116; 623/1.11–1.12
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,425,908 A | 1/1984 | Simon | |
| 4,643,184 A | 2/1987 | Mobin-Uddin | |
| 4,662,885 A | 5/1987 | DiPisa, Jr. | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,857,045 A | 8/1989 | Rydell | |
| 4,873,978 A | 10/1989 | Ginsburg | |
| 4,886,061 A | 12/1989 | Fischell et al. | |
| 4,969,891 A | 11/1990 | Gewertz | |
| 5,011,488 A | 4/1991 | Ginsburg | |
| 5,071,407 A | 12/1991 | Termin et al. | |
| 5,133,733 A | 7/1992 | Rasmussen et al. | |

(Continued)

FOREIGN PATENT DOCUMENTS

WO       96/01591 A1    1/1996

*Primary Examiner*—Todd E Manahan
*Assistant Examiner*—Christopher Schubert
(74) *Attorney, Agent, or Firm*—Crompton, Seager & Tufte LLC (57) ABSTRACT

Devices and methods for delivery or retrieval of a distal protection device. A distal protection assembly may comprise an outer sheath, an inner shaft disposed within a lumen of the outer sheath, a distal protection device disposed at a distal end of the inner shaft; and a manifold coupled to a proximal end of the outer sheath that is adapted for moving the outer sheath relative to the inner shaft.

14 Claims, 5 Drawing Sheets

U.S. PATENT DOCUMENTS

| | | |
|---|---|---|
| 5,160,342 A | 11/1992 | Reger et al. |
| 5,192,286 A | 3/1993 | Phan et al. |
| 5,290,310 A | 3/1994 | Makower et al. |
| 5,324,304 A | 6/1994 | Rasmussen |
| 5,324,306 A | 6/1994 | Makower et al. |
| 5,329,942 A | 7/1994 | Gunther et al. |
| 5,370,657 A | 12/1994 | Irie |
| 5,415,630 A | 5/1995 | Gory et al. |
| 5,419,774 A | 5/1995 | Willard et al. |
| 5,433,723 A | 7/1995 | Lindenberg et al. |
| 5,462,529 A | 10/1995 | Simpson et al. |
| 5,536,242 A | 7/1996 | Willard et al. |
| 5,549,626 A | 8/1996 | Miller et al. |
| 5,662,671 A | 9/1997 | Barbut et al. |
| 5,669,933 A | 9/1997 | Simon et al. |
| 5,681,347 A | 10/1997 | Cathcart et al. |
| 5,769,816 A | 6/1998 | Barbut et al. |
| 5,779,716 A | 7/1998 | Cano et al. |
| 5,800,457 A | 9/1998 | Gelbfish |
| 5,800,525 A | 9/1998 | Bachinski et al. |
| 5,807,398 A | 9/1998 | Shaknovich |
| 5,814,064 A | 9/1998 | Daniel et al. |
| 5,833,650 A | 11/1998 | Imran |
| 5,848,964 A | 12/1998 | Samuels |
| 5,906,619 A | 5/1999 | Olson et al. |
| 5,911,734 A | 6/1999 | Tsugita et al. |
| 5,928,264 A | 7/1999 | Sugarbaker et al. |
| 6,066,149 A | 5/2000 | Samson et al. |
| 6,066,158 A | 5/2000 | Engelson et al. |
| 6,142,987 A | 11/2000 | Tsugita |
| 6,152,946 A | 11/2000 | Broome et al. |
| 6,168,579 B1 | 1/2001 | Tsugita |
| 6,171,327 B1 | 1/2001 | Daniel et al. |
| 6,203,550 B1 | 3/2001 | Olson |
| 6,203,561 B1 | 3/2001 | Ramee et al. |
| 6,206,868 B1 | 3/2001 | Parodi |
| 6,221,006 B1 | 4/2001 | Dubrul et al. |
| 6,277,139 B1 | 8/2001 | Levinson et al. |
| 6,355,051 B1 | 3/2002 | Sisskind et al. |
| 6,533,772 B1 | 3/2003 | Sherts et al. |
| 6,605,102 B1 | 8/2003 | Mazzocchi et al. |
| 6,669,716 B1 | 12/2003 | Gilson et al. |
| 6,685,722 B1 | 2/2004 | Rosenbluth et al. |
| 6,755,854 B2 | 6/2004 | Gillick et al. |
| 2002/0128679 A1 | 9/2002 | Turovskiy et al. |

DELIVERY AND RETRIEVAL MANIFOLD FOR A DISTAL PROTECTION FILTER

RELATED APPLICATIONS

This application is a continuation application of U.S. application Ser. No. 10/053,143, filed Jan. 17, 2002.

BACKGROUND OF THE INVENTION

1. Field of the Invention

The present invention relates generally to devices and methods for treating occluded or stenoic blood vessels. More particularly, the present invention relates to devices and methods for using and retrieving a distal protection device from the vasculature of a patient.

2. Description of the Related Art

Atherosclerosis and other forms of vascular disease are a major health problem in the United States and the world. Generally, vascular disease results in blood vessels becoming blocked or narrowed. This blockage can result in a lack of oxygen for the heart. It is critical that the heart muscle be well oxygenated so that the blood pumping action of the heart is not impaired.

Occluded or stenotic blood vessels may be treated with a number of medical procedures including percutaneous transluminal angioplasty (PTA), percutaneous transluminal coronary angioplasty (PTCA), and atherectomy. These treatments are relatively non-invasive methods of treating a stenotic lesion. Angioplasty techniques typically involve the use of a balloon catheter. The balloon catheter is advanced over a guidewire such that the balloon is positioned adjacent a stenotic lesion. The balloon is then inflated and the stenosis is expanded. During an atherectomy procedure, the stenotic lesion is typically mechanically cut away from the blood vessel wall.

During angioplasty and atherectomy procedures, stenotic debris is often separated from the stenosis and may be free to flow within the lumen of the vessel. If this debris enters the circulatory system, it could block other vascular regions including the neural vasculature or in the lungs. During angioplasty procedures, stenotic debris may also break loose due to manipulation of the blood vessel. Because of this debris, a number of devices termed distal protection devices have been developed to filter out this debris.

Before using a distal protection device, the device will need to be delivered to an area downstream of where treatment will take place. It is important that the device be delivered properly and efficiently. A need, therefore, exists for devices for delivery of distal protection devices.

After an intravascular procedure has been performed, the distal protection device will need to be removed from the vasculature. Because the distal protection devices are typical used in an expanded condition, it may be difficult to remove the device. A need, therefore exists for devices suitable for retrieval of distal protection devices.

BRIEF SUMMARY OF THE INVENTION

The present invention pertains to a novel distal protection assembly for delivering or retrieving a distal protection filter. A distal protection assembly may comprise an outer sheath, an inner shaft disposed within a lumen of the outer sheath, a distal protection device coupled to a distal end of the inner shaft, and a manifold coupled to the outer sheath. The manifold may include an actuation assembly that, when actuated, may result in movement of the outer sheath relative to the inner shaft. This movement will shift the filter between a delivered position and a retrieved position.

The manifold may comprise a proximal end, a distal end, a handle region, an opening located between the proximal end and the distal end, and may include a rail. An actuator assembly may be disposed at the opening. The actuator assembly may comprise a button having a proximal end, a distal end, and a lumen extending therethrough. The proximal end of the outer sheath is coupled to the distal end of the button. The button may be longitudinally movable along the rail such that movement of the button results in a substantially similar movement of the outer sheath relative to the inner shaft. The manifold may, thus, be actuated to shift the distal protection device between a delivery position and a retrieval position by longitudinal movement of the button.

Alternatively, the outer sheath may further comprise or be coupled to a proximal tubular member. The proximal tubular member may further comprise teeth. The actuator assembly may comprise a gear coupled to a thumbwheel, or one or more buttons. The teeth may engage the gear so that rotation of the thumbwheel, or pressing or rotating a button may result in movement of the outer sheath relative to the inner shaft.

DETAILED DESCRIPTION OF THE INVENTION

The following description should be read with reference to the drawings wherein like reference numerals indicate like elements throughout the several views. The detailed description and drawings illustrate example embodiments of the claimed invention.

Figure 1:
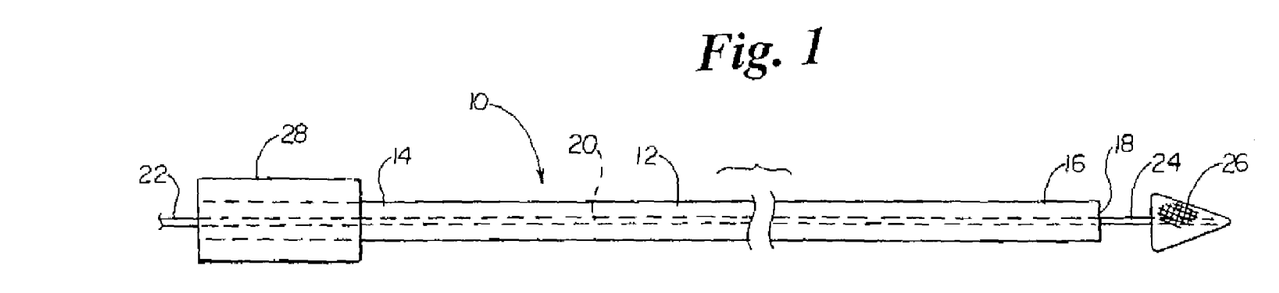
FIG. 1 is plan overview of a distal protection assembly.

When delivering or retrieving a distal protection filter, it may be important to secure the position of the filter (or filter wire) relative to a delivery or retrieval sheath. This may allow a clinician to accurately deliver or retrieve the filter and minimize unwanted or unplanned movement thereof. FIG. 1 is a plan overview of a distal protection assembly 10. Distal protection assembly 10 includes an outer sheath 12 having a lumen 18, an inner shaft 20 disposed within lumen 18, a distal protection filter 26 coupled to inner shaft 20, and a manifold 28 coupled to a proximal end 14 of outer sheath 12. Manifold 28 may be used to actuate sheath 12 relative to shaft 20 in order to deliver or retrieve filter 26. In this embodiment manifold 28 is shown systematically, in the subsequently described manifold embodiments a detailed description is provided, Outer sheath 12 having proximal end 14, a distal end 16, and lumen 18 extending therethrough may be comprised of materials including, but not limited to, metals, stainless steel, nickel alloys, nickel-titanium alloys, thermoplastics, high performance engineering resins, fluorinated ethylene propylene (FEP), polymer, polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polycarbonate, acrylonitrile butadiene styrene (ABS), etc.

At least a portion of inner shaft 20 may be disposed within lumen 18. Inner shaft 20 includes a proximal end 22 and a distal end 24. Inner shaft 20 may be comprised of materials similar to those listed above. For example, inner shaft 20 may comprise a stainless steel or nickel-titanium alloy guidewire.

Distal protection filter 26 may be disposed at distal end 24 of inner shaft 20. Filter 26 may be comprised of a polyurethane sheet and include at least one opening that may be, for example, formed by known laser techniques. The holes or openings are sized to allow blood flow therethrough but restrict flow of debris or emboli floating in the body lumen or cavity. Filter 26 may be generally cone-shaped, and have a proximal and a distal end. The distal end may be a narrow, "V"-shaped end and is fixedly secured or formed to shaft 26. The proximal end has a relatively wide opening. Alternatively, filter 26 may be cylindrical with a relatively rounded distal end.

Filter 26 operates between a closed collapsed profile and an open radially-expanded deployed profile for collecting debris in a body lumen. Filter 26 may include a collapsible proximally-tapered frame having a mouth and a plurality of longitudinally-extending ribs. In an expanded profile, the mouth is opened and the ribs extend radially outwardly to support the mouth. In an alternate embodiment, filter 26 may comprise a number of differing objects including, but not limited to, a filter, a basket, a filter basket, a sheath, a capture sheath, a capturing device, one or more struts, one or more ribs, a mesh, a net, an expandable object, a self-expanding object, and combinations thereof. A number of differing configurations of filter 26 may be substituted without departing from the spirit of the invention.

Manifold 28 may be polymeric or, for example, be comprised of materials similar to those listed above. Outer sheath 12 may be coupled to manifold 28. For example, outer sheath 12 may be coupled to an actuation assembly of manifold 28 such that outer sheath 12 is movable relative to inner shaft 20 by actuating the actuation assembly. Examples of mechanisms for moving outer sheath 12 are described below. Inner shaft 20 may also be coupled to manifold 28. For example, inner shaft 20 may pass through an opening or lumen within manifold 28. In addition, shaft 20 may be fixed relative to manifold 28 by a collet 149 (please see FIG. 4) or other suitable structures.

Figure 2:
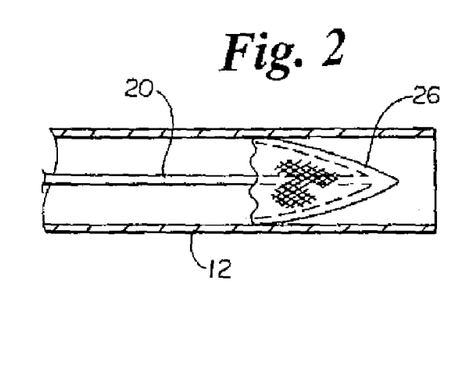
FIG. 2 is an enlarged view of a distal protection device of FIG. 1 in a retrieved position.

Filter 26 may be delivered or retrieved by actuating manifold 28 to move outer sheath 12 relative to inner shaft 20. Filter 26 is understood to be retrieved when it is collapsed and wherein at least a portion thereof is contained within outer sheath 12. FIG. 2 is an enlarged view of filter 26 in a retrieved position. Retrieval results in distal protection filter 26 being in a configuration suitable for removal from the vasculature.

Figure 3:
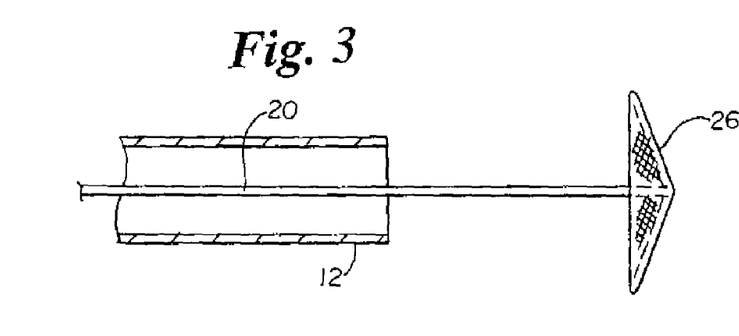
FIG. 3 is an enlarged view of a distal protection device of FIG. 1 in a delivered position.

Filter 26 is understood to be delivered when it is expanded and wherein at least a portion of thereof is not contained within outer sheath 12. FIG. 3 is an enlarged view of filter 26 in a delivered position. Delivery results in filter 26 being in a configuration within the vasculature suitable for collecting intravascular debris.

Figure 4:
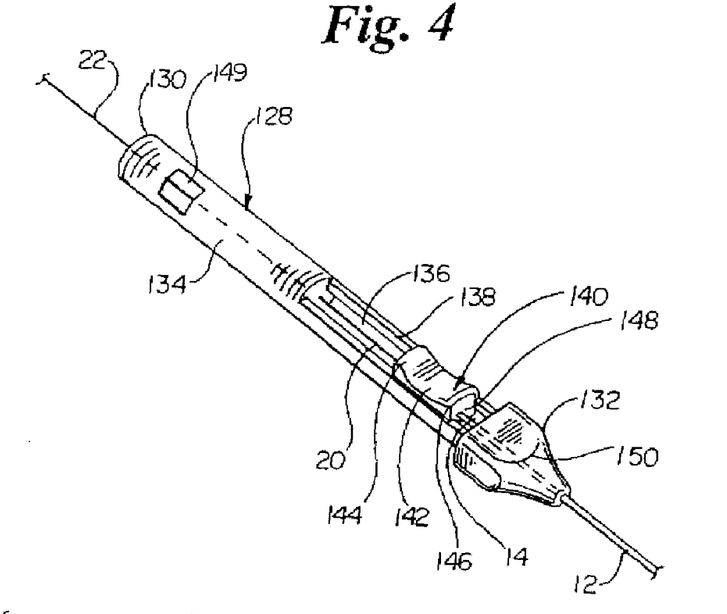
FIG. 4 is a perspective view of a manifold.

FIG. 4 is a perspective view of manifold 128 according to an embodiment of the invention. Similar to what is disclosed above, actuation of manifold 128 may result in movement of outer sheath 12 relative to inner shaft 20. This actuation may shift filter 26 between a delivery position and a retrieval position.

Manifold 128 may comprise a proximal end 130, a distal end 132, and a handle region 134. Handle region 134 is sized appropriately for a person's hand to hold and be able to actuate manifold 128. Manifold 128 may further comprise an opening 136 located between proximal end 130 and distal end 132. In an exemplary embodiment, opening 136 may further comprise a rail 138.

An actuator assembly 140 may be disposed at opening 136. Actuator assembly 140 may comprise a button 142 having a proximal end 144, a distal end 146, and a lumen 148 extending therethrough. Button 142 may comprise a number of shapes including symmetric, flat, concave, etc. Proximal end 14 of outer sheath 12 is coupled to distal end 146 of button 142. For example, outer sheath 12 may be secured to actuator assembly 140 by adhesive or heat bonding techniques.

Proximal end 22 of inner shaft 20 may pass through lumen 148. In an exemplary embodiment, proximal end 22 of inner shaft 20 passes through lumen 148, through proximal end 144 of button 142, is secured to manifold 128 proximate to proximal end 130 of manifold 128 by a collet 149, and may extend out of proximal end 130 of manifold 128. According to this embodiment, manifold 128 may be used as a subassembly for a number of different over-the-wire catheters.

Button 142 may be longitudinally movable along rail 138. Because outer sheath 12 is coupled to distal end 146 of button 142, movement of button 142 results in a substantially similar movement of outer sheath 12 relative to inner shaft 20. Movement of button 142 in the proximal direct may, for example, move outer sheath 12 proximally to shift filter 26 into a delivered position. Analogously, distal movement of button 142 may move outer sheath 12 distally and shift filter 26 into a retrieved position. It should be appreciated that the direction of motion required to shift the relative position of filter 26 relative to sheath 12 may be altered without departing from the scope of the invention.

Figure 5:
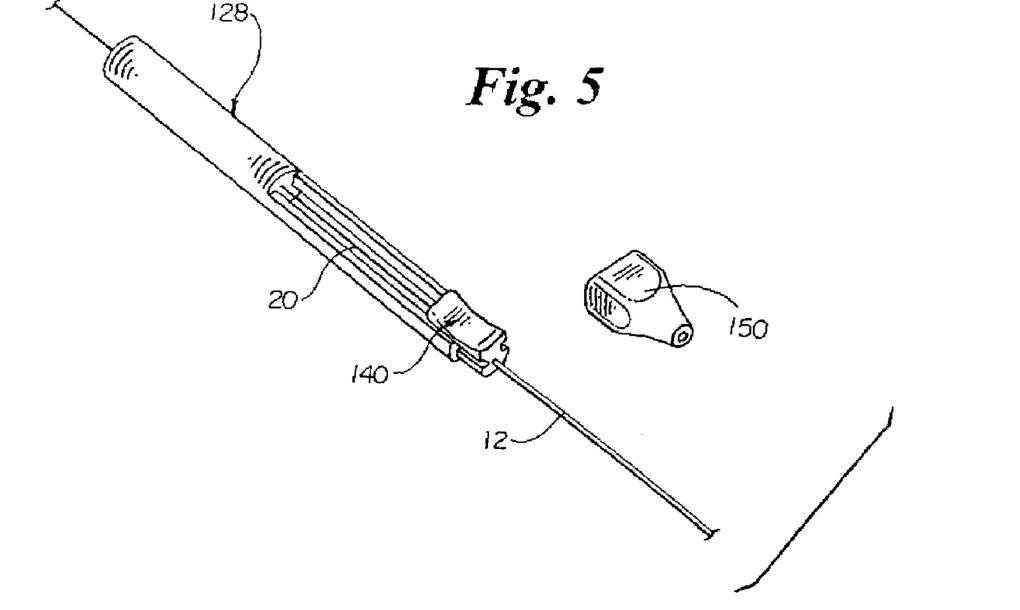
FIG. 5 is a perspective view of the manifold of FIG. 4, wherein the actuator retention cover is removed.

Distal end 132 of manifold 128 may further comprise an actuator retention cover 150. Actuator retention cover 150 holds button 142 in position and may allow for only the desired motion of button 142. FIG. 5 is a perspective view of manifold 128 with actuator retention cover 150 removed.

In an alternate embodiment, outer sheath 12 may be fixed relative to manifold 128 and inner shaft 20 may be coupled to actuator assembly 140. According to this embodiment, longitudinal movement of button 142 would move inner shaft 20 relative to outer sheath 12. This embodiment may be particularly important if a specific direction of actuation (e.g., actuating button 142 proximally or distally) is preferred by a clinician.

Figures 6, 7:
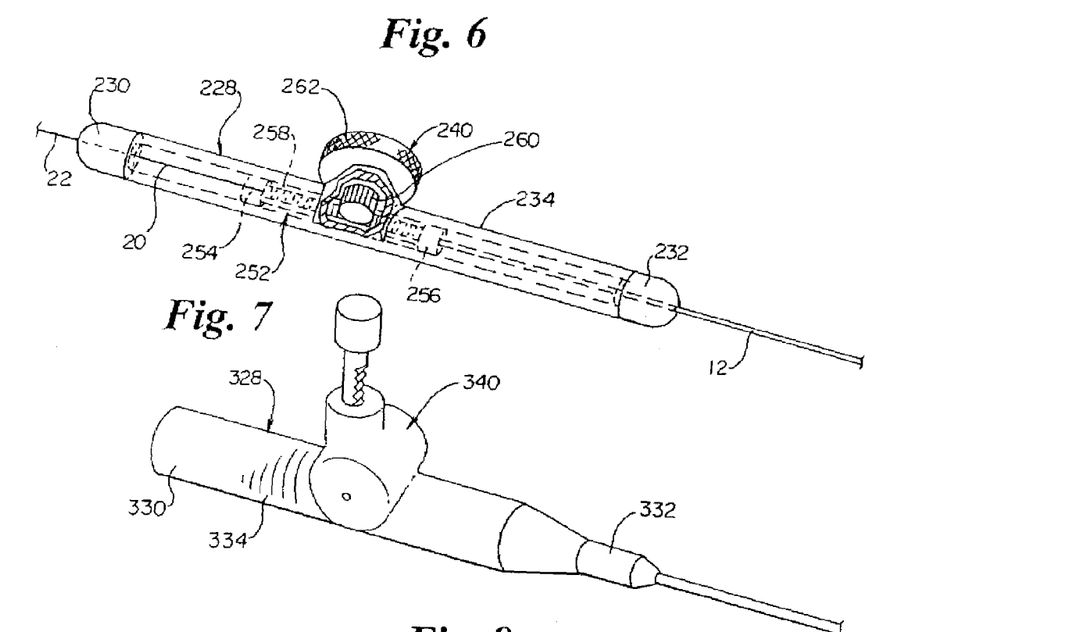
FIG. 6 is a perspective view of an alternative embodiment of a manifold.
FIG. 7 is a perspective of a second alternative embodiment of a manifold.

FIG. 6 is a perspective view of an alternative embodiment of a manifold according to an embodiment of the invention. Manifold 228 may comprise proximal end 230, distal end 232, and handle region 234 sized appropriately for a person's hand to hold and be able to actuate manifold 228.

Outer sheath 12 may further comprise or be coupled to a proximal tubular member 252. Proximal tubular member 252 may include a proximal end 254 and a distal end 256. Proximal tubular member 252 may be slidably disposed within manifold 228. Proximal end 254 and distal end 256 of proximal tubular member 252 may prevent excessive movement (i.e., movement in excess of what is required to deliver or retrieve filter 26) of outer sheath 12 relative to inner shaft 20 and manifold 228.

Proximal end 22 of inner shaft 20 may pass through proximal tubular member 252 and may extend through proximal end 230 of manifold 228. In an exemplary embodiment, proximal end 22 of inner shaft 20 passes through proximal tubular member 252 and is secured to manifold 228 proximate to proximal end 230 of manifold 228, for example by a collet.

Proximal tubular member 252 may further comprise teeth 258 and actuator assembly 240 may comprise a gear 260 coupled to a thumbwheel 262. Teeth 258 may engage gear 260 of actuator assembly 240. Rotation of thumbwheel 262, thus, may result in rotation of gear 260 and movement of outer sheath 12 relative to inner shaft 20. According to this embodiment, manifold 228 may be actuated to shift filter 26 between a delivery position and a retrieval position by rotation of thumbwheel 262.

FIG. 7 is a perspective view of a second alternative embodiment of a manifold according to an embodiment of the invention. Similar to what is disclosed above, manifold 328 may comprise proximal end 330, distal end 332, handle region 334, and actuation assembly 340.

Figure 8:
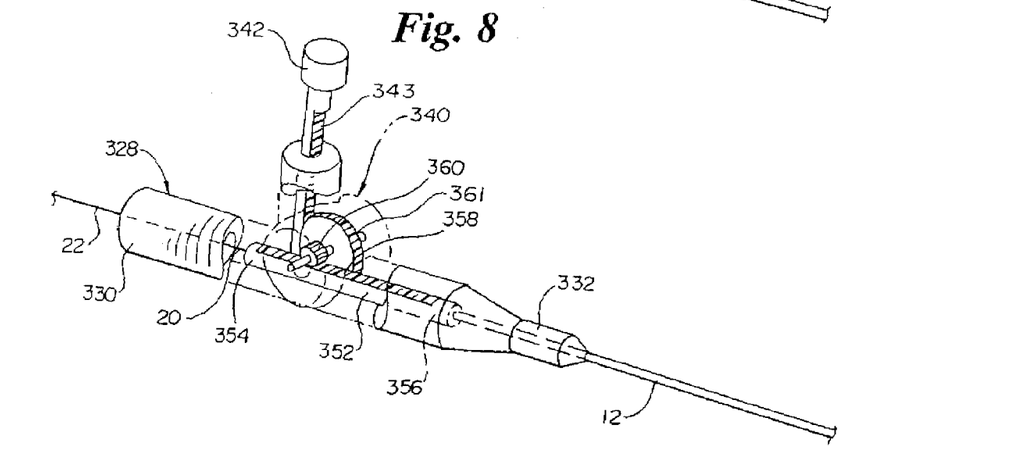
FIG. 8 is a perspective view of the manifold shown in FIG. 7.

FIG. 8 is perspective view of manifold 328. Similar to what is disclosed above, outer sheath 12 may further comprise or be coupled to proximal tubular member 352 having proximal end 354, distal end 356, and teeth 358. Proximal end 22 of inner shaft 20 may pass through proximal tubular member 352 and be secured to manifold 328 proximate to proximal end 330 of manifold 328.

Actuator assembly 340 may comprise gear 360 coupled to button 342. Teeth 358 may engage gear 360 of actuator assembly 340. Pressing button 342 may result in rotation of gear 360 that can ultimately result in movement of outer sheath 12 relative to inner shaft 20. According to this embodiment, manifold 328 may be actuated to shift filter 26 between a delivery position and a retrieval position by pressing button 342.

Button 342 includes teeth 343 that engage a second gear 361 that is coupled to gear 360. According to this embodiment, pressing button 342 results in movement of second gear 361, which subsequently results in movement of gear 360. Including more than one gear allows a designer to alter the gear configurations in order to set the desired mechanical properties of assembly 340. For example, increasing the diameter of gear 361 relative to gear 360 may increase the mechanical advantage of assembly 340. Similarly, altering the gear ratios of gears 360,361 may also result in an increased mechanical advantage. A number of different configurations of gears 360,361 may be used in this and other similar embodiments without departing from the spirit of the invention.

In use, it may be understood that pressing button 342 may result in movement of outer sheath 12 in only a single direction depending on the configuration of gear 360. For example, FIG. 8 depicts gear 360 configured such that pressing button 342 results in distal movement of outer sheath 12 so as to shift filter 26 to the retrieved position. Alternatively, FIG. 9 depicts an alternative manifold 428 wherein pressing of button 442 results in proximal movement of outer sheath 12 so as to shift filter 26 to the delivered position.

Figure 9:
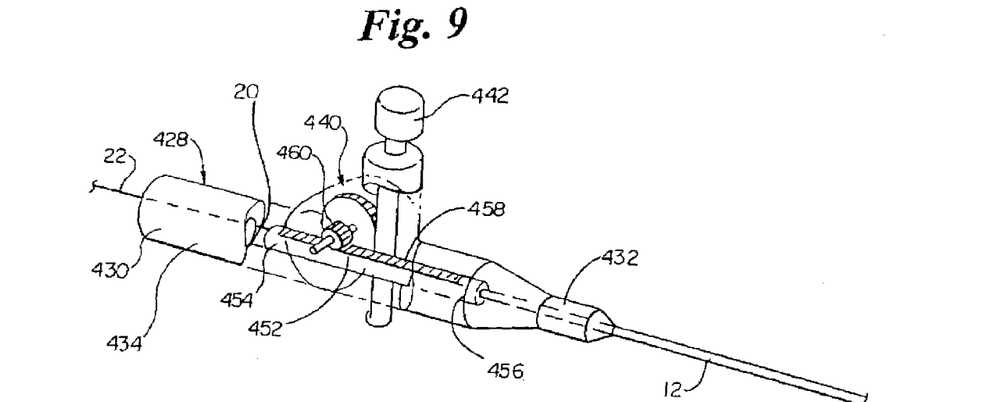
FIG. 9 is a perspective view of an alternative embodiment of the manifold shown in FIG. 7.

According to the embodiment shown in FIG. 9, manifold 428 may comprise proximal end 430, distal end 432, and handle region 434. Outer sheath 12 may further comprise or be coupled to proximal tubular member 452 having proximal end 454, distal end 456, and teeth 458. Proximal end 22 of inner shaft 20 may pass through proximal tubular member 452 and be secured to manifold 428 proximate to proximal end 430 of manifold 428 in a manner similar to those described above.

Actuator assembly 440 may comprise gear 460 coupled to button 442. Teeth 458 may engage gear 460 of actuator assembly 440 so that pressing button 442 may result in rotation of gear 460 that can ultimately result in movement of outer sheath 12 proximally relative to inner shaft 20.

Figure 10:
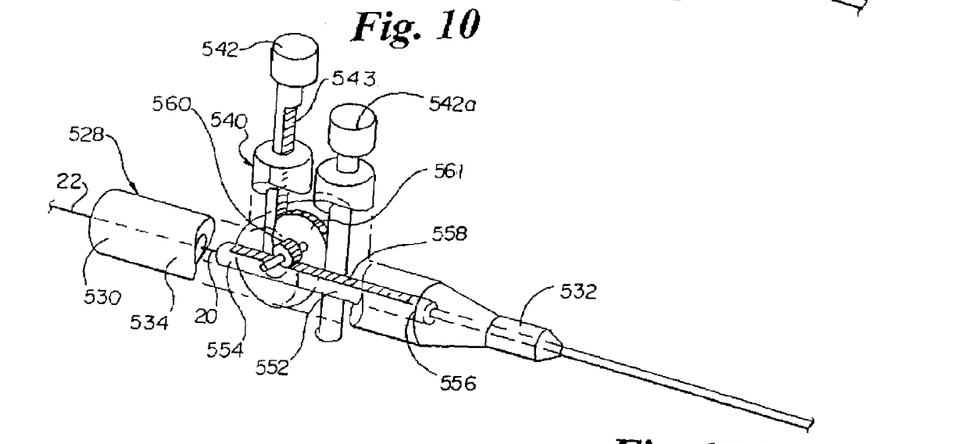
FIG. 10 is a perspective view of a second alternative embodiment of the manifold shown in FIG. 7.

FIG. 10 is a perspective view of a third alternative embodiment of manifold 528 according to an embodiment of the invention. Similar to what is disclosed above, manifold 528 may comprise proximal end 530, distal end 532, and handle region 534.

Outer sheath 12 may further comprise or be coupled to proximal tubular member 552 having proximal end 554, distal end 556, and teeth 558. Actuator assembly 540 may comprise gear 560 coupled to button 542 by a second gear 561. Teeth 558 may engage gear 560 of actuator assembly 540 so that pressing button 542 may result in rotation of gear 560 that can ultimately result in movement of outer sheath 12 relative to inner shaft 20. Similar to what is described above, button 542 includes teeth 543 that engage a second gear 561 such that pressing button 542 results in movement of second gear 561, which subsequently results in movement of gear 560.

Actuator assembly 540 further comprises a second button 542a. Button 542a includes teeth (not shown, but essentially the same as teeth 543) that engage second gear 561 so that pressing button 542a results in rotation of gear 561 and gear 560 that ultimately results in movement of outer sheath 12 relative to inner shaft 20 in a direction that is opposite to pressing button 542. According to this embodiment, manifold 528 comprises the ability to shift filter 26 to either the delivery position or the retrieval position depending on whether button 542 or 542a is pressed.

Figures 11, 11A:
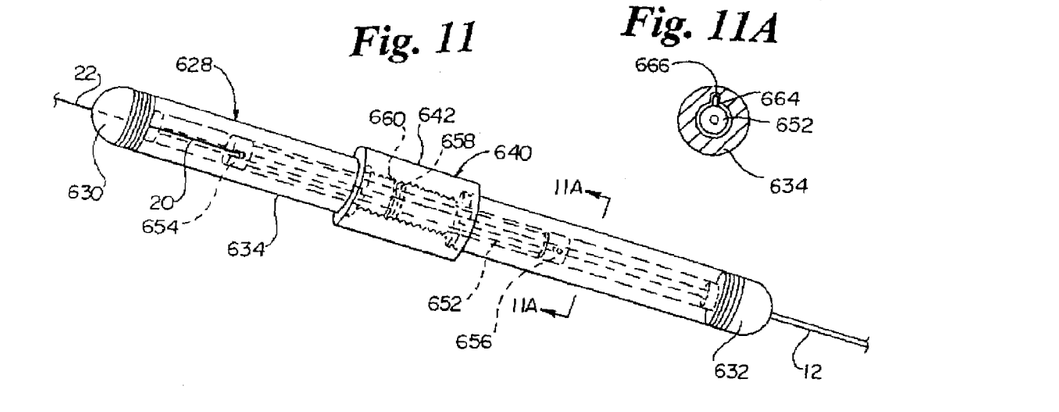
FIG. 11 is a perspective view of a third alternative embodiment of a manifold.
FIG. 11A is an enlarged view through section 11A-11A.

FIG. 11 is a perspective view of a third embodiment of a manifold according to an embodiment of the invention. Similar to what is disclosed above, manifold 628 may comprise proximal end 630, distal end 632, and handle region 634.

Outer sheath 12 may further comprise or be coupled to proximal tubular member 652 having proximal end 654, distal end 656, and teeth 658. Actuator assembly 640 may comprise gear 660 coupled to button 642 that is axially rotatable. Teeth 658 may engage gear 660 of actuator assembly 640. Axial rotation of button 642 may result in movement of outer sheath 12 relative to inner shaft 20. According to this embodiment, manifold 628 may be actuated to shift filter 26 between a delivery position and a retrieval position by rotation button 642.

FIG. 11A is a cross-sectional view of manifold 628 taken through line 11A-11A. According to this embodiment, proximal tubular member 652 may further comprise a key 664 adapted to engage a notch 666 handle region 634. Key 664 may substantially prevent axial rotation of proximal tubular member 652 when actuator assembly 640 is rotated. Rotation of proximal tubular member 652 may interfere with the movement of outer sheath 12 relative to inner shaft 20.

Figure 12:
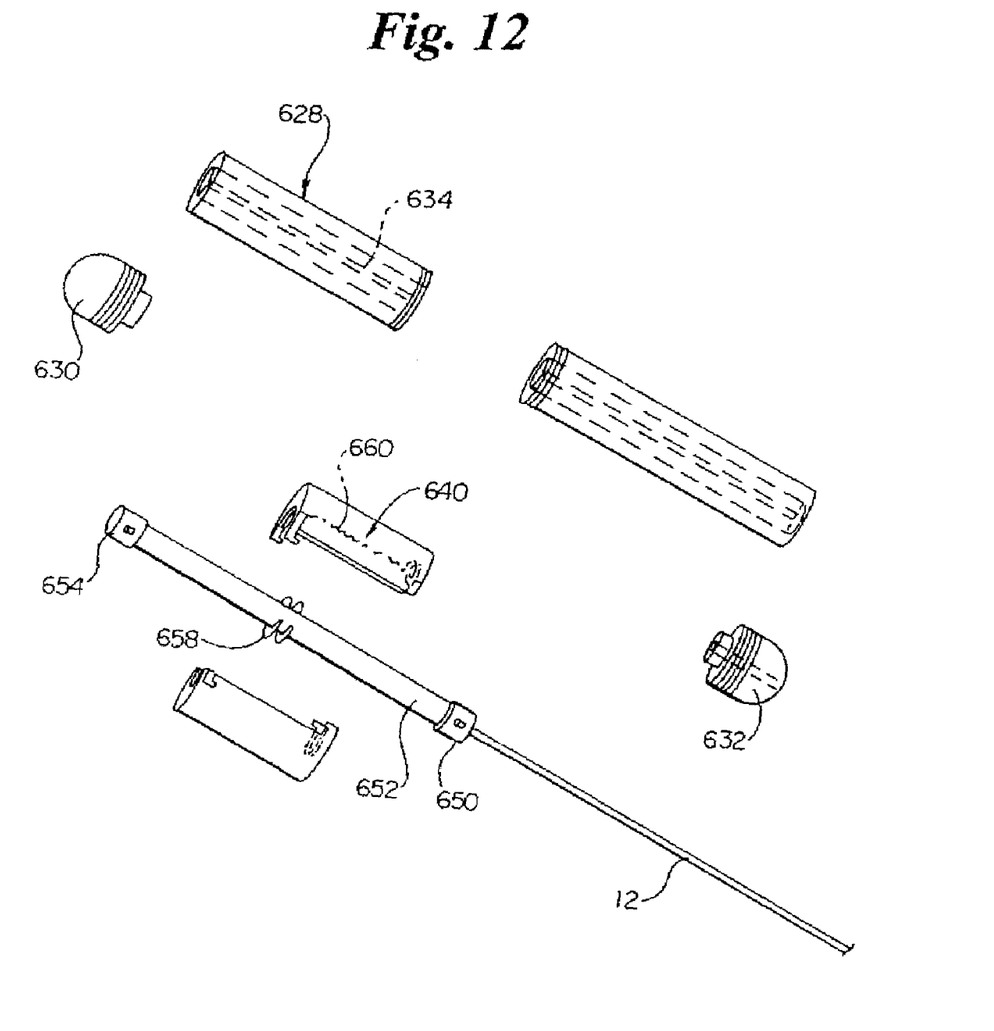
FIG. 12 is an exploded view of the manifold of FIG. 11, wherein the actuator assembly is removed.

FIG. 12 is an exploded view of manifold 628 wherein actuator assembly 640 has been removed. FIG. 12 is provided so as to more clearly illustrate the elements of manifold 628.

Numerous advantages of the invention covered by this document have been set forth in the foregoing description. It will be understood, however, that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A distal protection assembly, comprising:
   an outer sheath having a proximal end, a distal end, and a lumen extending therethrough;
   an inner shaft disposed within the lumen, the inner shaft having a proximal end and a distal end;
   a distal protection device disposed at the distal end of the inner shaft;
   a manifold coupled to the proximal end of the inner shaft, the manifold including an actuator assembly; and
   the actuator assembly coupled to the proximal end of the outer sheath and capable of moving the outer sheath relative to the inner shaft, the actuator assembly includes a first button and a second button;
   wherein the actuator assembly is configured such that pressing the first button moves the outer sheath relative to the inner shaft in a first direction and pressing the second button moves the outer sheath relative to the inner shaft in a second direction opposite to the first direction.

2. The distal protection assembly of claim 1, wherein the distal protection device comprises a filter.

3. The distal protection assembly of claim 1, wherein the distal protection device comprises a mesh.

4. The distal protection assembly of claim 1, wherein the distal protection device comprises a strut.

5. The distal protection assembly in accordance with claim 1, wherein the distal protection device comprises a rib.

6. The distal protection assembly of claim 1, further comprising an actuator retention cover.

7. The distal protection assembly of claim 1, wherein the actuator assembly includes a first gear that interacts with the first button and a second gear that interacts with the second button.

8. The distal protection assembly of claim 1, wherein pressing the first button moves the outer sheath proximally relative to the inner shaft.

9. The distal protection assembly of claim 1, wherein pressing the second button moves the outer sheath distally relative to the inner shaft.

10. A method of actuating a distal protection assembly, comprising the steps of:
    providing a distal protection assembly including an outer sheath having a proximal end, a distal end, and a lumen extending therethrough; an inner shaft disposed within the lumen, the inner shaft having a proximal end and a distal end; a distal protection device disposed at the distal end of the inner shaft; a manifold coupled to the proximal end of the inner shaft, a proximal tubular member including teeth, the proximal tubular member disposed within at least a portion of the manifold and coupled to the proximal end of the outer sheath; the manifold including an actuator assembly; and the actuator assembly coupled to the proximal tubular member and capable of moving the outer sheath relative to the inner shaft, the actuator assembly including includes a first button and a second button;
    wherein the actuator assembly is configured such that pressing the first button moves the outer sheath relative to the inner shaft in a first direction and pressing the second button moves the outer sheath relative to the inner shaft in a second direction opposite to the first direction.
    actuating the actuator assembly by pressing one of the first button and the second button; and
    wherein actuating the actuator assembly shifts the distal protection device between a delivery position and a retrieval position.

11. The method of claim 10, wherein the step of actuating the actuator assembly further comprises collapsing the distal protection device.

12. The method of claim 10, wherein the step of actuating the actuator assembly further comprises expanding the distal protection device.

13. The method of claim 10, wherein pressing the first button results in the outer sheath moving proximally relative to the inner shaft.

14. The method of claim 10, wherein pressing the second button results in the outer sheath moving distally relative to the inner shaft.

* * * * *